(12) United States Patent
Mori et al.

(10) Patent No.: US 6,978,172 B2
(45) Date of Patent: Dec. 20, 2005

(54) METHOD FOR IN VIVO DELIVERY OF THERAPEUTIC AGENTS

(75) Inventors: Kenji Mori, San Diego, CA (US); Iwao Nozawa, Carlsbad, CA (US); Shuji Sato, Chiba (JP)

(73) Assignee: Hisamitsu Pharmaceutical Co., Inc., (JP)

( * ) Notice: Subject to any disclaimer, the term of this patent is extended or adjusted under 35 U.S.C. 154(b) by 61 days.

(21) Appl. No.: 10/335,641

(22) Filed: Dec. 30, 2002

(65) Prior Publication Data

US 2003/0097090 A1 May 22, 2003

Related U.S. Application Data

(62) Division of application No. 08/964,872, filed on Nov. 5, 1997, now Pat. No. 6,775,569.

(51) Int. Cl.⁷ .............................................. A61N 1/30
(52) U.S. Cl. ..................................................... 604/20
(58) Field of Search ........................ 604/20–21, 96.01; 435/285.2, 173.6

(56) References Cited

U.S. PATENT DOCUMENTS

| | | | |
|---|---|---|---|
| 4,211,222 A | 7/1980 | Tapper ........................ 128/207 |
| 4,474,570 A | 10/1984 | Ariura et al. | |
| 4,820,263 A | 4/1989 | Spevak et al. ................. 604/20 |
| 5,002,527 A | 3/1991 | Reller et al. ................... 604/20 |
| 5,006,108 A | 4/1991 | LaPrade ....................... 604/20 |
| 5,053,001 A | 10/1991 | Reller et al. ................... 604/20 |
| 5,128,257 A | 7/1992 | Baer .......................... 435/173 |
| 5,250,023 A | 10/1993 | Lee et al. ..................... 604/20 |
| 5,298,017 A | 3/1994 | Theeuwes et al. ............. 604/20 |
| 5,304,120 A | 4/1994 | Crandell et al. | |
| 5,318,514 A | 6/1994 | Hofmann | |
| 5,322,502 A | 6/1994 | Theeuwes et al. | |
| 5,387,189 A | 2/1995 | Gory et al. .................... 604/20 |
| 5,389,069 A | 2/1995 | Weaver ........................ 604/21 |
| 5,464,386 A | 11/1995 | Hofmann | |
| 5,507,724 A * | 4/1996 | Hofmann et al. ........... 604/501 |
| 5,520,180 A | 5/1996 | Uy et al. ..................... 128/640 |
| 5,533,971 A | 7/1996 | Phipps ........................ 604/20 |
| 5,558,632 A | 9/1996 | Lloyd et al. ................... 604/20 |
| 5,573,503 A | 11/1996 | Untereker et al. | |
| 5,582,587 A | 12/1996 | Gyory et al. .................. 604/20 |
| 5,601,618 A | 2/1997 | James | |
| 5,620,580 A | 4/1997 | Okabe et al. | |
| 5,624,415 A | 4/1997 | Cormier et al. ............. 604/290 |
| 5,651,768 A | 7/1997 | Sibalis | |
| 5,668,170 A | 9/1997 | Gyory ........................ 514/449 |
| 5,676,648 A | 10/1997 | Henley ........................ 604/20 |
| 5,678,545 A | 10/1997 | Stratbucker | |
| 5,688,233 A | 11/1997 | Hofmann et al. ............. 604/20 |
| 5,697,896 A | 12/1997 | McNichols et al. ........... 604/20 |
| 5,700,481 A | 12/1997 | Iga et al. ..................... 424/449 |

(Continued)

FOREIGN PATENT DOCUMENTS

WO    WO 89/06555    7/1989

*Primary Examiner*—LoAn H. Thanh
(74) *Attorney, Agent, or Firm*—Fish & Richardson P.C.

(57) ABSTRACT

Electroporation electrodes are laminated to a permeable membrane to form an electrode membrane. Such an electrode membrane is useful for a continuous controlled delivery of a therapeutic agent through the skin or mucosa, when placed in direct contact with the skin or mucosa and by application of electric field pulses at specified intervals. An electrode membrane can be assembled such that it incorporates an iontophoretic electrode in the same device. This device can be jointly utilized for electroporation and iontophoretic drug delivery through the skin and mucosal membrane.

12 Claims, 3 Drawing Sheets

U.S. PATENT DOCUMENTS

| | | |
|---|---|---|
| 5,704,908 A * | 1/1998 | Hofmann et al. .............. 604/21 |
| 5,817,044 A | 10/1998 | Evers et al. .................. 604/20 |
| 5,843,014 A | 12/1998 | Lattin et al. |
| 5,843,015 A | 12/1998 | Sage, Jr. et al. .............. 604/20 |
| 5,938,658 A | 8/1999 | Tu .............................. 606/41 |
| 5,968,005 A | 10/1999 | Tu .............................. 604/20 |
| 5,983,131 A | 11/1999 | Weaver et al. ................ 604/20 |
| 6,009,345 A | 12/1999 | Hofmann |
| 6,104,952 A | 8/2000 | Tu et al. ....................... 604/20 |
| 6,748,265 B2 * | 6/2004 | Hofmann et al. ............. 604/20 |

* cited by examiner

METHOD FOR IN VIVO DELIVERY OF THERAPEUTIC AGENTS

CROSS-REFERENCE TO RELATED APPLICATIONS

This application is a divisional of U.S. patent application Ser. No. 08/964,872, filed Nov. 5, 1997 now U.S. Pat. No. 6,775,569.

TECHNICAL FIELD

The invention relates to delivery of therapeutic agents, and more particularly to a method and apparatus for in vivo delivery of therapeutic agents through the skin or mucosa using an electromotive force such as electroporation or iontophoresis.

BACKGROUND INFORMATION

Electroporation, which includes electropermealization, involves the creation of aqueous pathways in lipid bilayer membranes by the application of a brief electric field pulse. Electroporation has found wide-spread application in molecular biology and in transgenics as a method of introducing DNA or other material to a cell by momentarily charging the cell with a high voltage. In recent years, this technique has also been applied to the delivery of therapeutic agents through skin or mucosa. A pore or opening is created in the skin or mucosa by an electric field created by the positive and negative differential between two electrodes. This reversible path or route (pore) created using electroporation increases the membrane (skin, mucosa) penetration of a substance. However, there have been problems in placing electrodes and establishing the proper relationship between the position of the electrodes.

In addition, multiple administrations have required multiple applications of electrodes and therapeutic agents, entailing repeated affixing and removing of electrodes, thereby irritating the site tissue. Similarly, delivery of therapeutic agents over a long period of time or multiple applications of voltage have required multiple alternating applications of electrodes and therapeutic agents. In constructing an actual device, difficulties have arisen in containing the therapeutic agents on the surface of the electrodes and in placing the surface containing therapeutic agents and the surface of the electrodes in direct contact with the skin. Thus, conventional devices which use electroporation have unresolved problems.

It is known that it is possible to further increase the permeation of therapeutic agents using electroporation and iontophoresis jointly. Iontophoresis uses electrical current to activate and to modulate the diffusion of a charged molecule across a biological membrane, such as the skin, in a manner similar to passive diffusion under a concentration gradient, but at a facilitated rate. In general, iontophoresis technology uses an electrical potential or current across a semipermeable barrier using an iontophoretic electrode pair, an iontophoretic electrode (anode or cathode) and a counter electrode. To jointly use electroporation and iontophoresis, an iontophoretic electrode must be placed in the same compartment (in the same device) as an electroporation electrode pair. While there are examples of in vitro experiments using electroporation and iontophoresis jointly, conventional techniques have not been able to create a device which can practically jointly use both types of electrodes.

Accordingly the inventor has determined that it would be desirable to have a method or device which would provide the following capabilities not provided by conventional techniques:
(1) simple administration of therapeutic agents using an electroporation electrode pair via skin or mucosa;
(2) application of electrodes for long periods of time and application of voltage multiple times without requiring multiple applications and removals of electrodes;
(3) simultaneous application of electric field pulses for electroporation and a pharmaceutical composition containing a therapeutic agent; and
(4) joint utilization of electroporation and iontophoretic electrodes.

The present invention provides such capabilities.

SUMMARY

A permeable membrane which is porous and is used to support electrodes for electroporation is useful for substantially continuous controlled delivery of a therapeutic agent through the skin or mucosa, when placed in direct contact with the skin or mucosa and by application of electric field pulses at specified intervals. The electroporation electrodes can be affixed to this porous membrane to form an electrode membrane. In addition, an electrode membrane can be assembled such that it can incorporate an iontophoretic electrode in the same device. This device can be jointly utilized for electroporation and iontophoresis. In addition, a device which has this kind of electrode membrane is practically useful and easily manufactured.

DESCRIPTION OF DRAWINGS

Like reference numbers and designations in the various Drawings indicate like elements.

DETAILED DESCRIPTION

Figure 1:
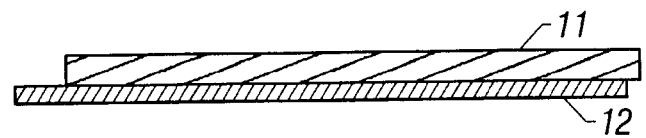
FIG. 1 shows a side view of a device according to a first embodiment of the invention.
Figure 2:
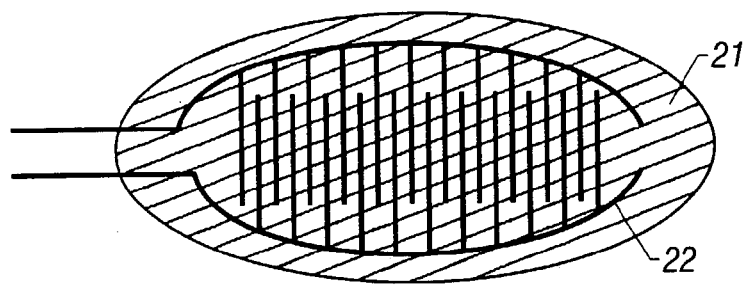
FIG. 2 shows a planar view of a device according to a first embodiment of the invention.

The structure and operational parameters of preferred embodiments of the invention will be explained below making references to the Drawings. FIGS. 1 and 2 show a device according to one embodiment of the invention. FIG. 1 is a side view of the device. FIG. 2 is a planar view of the same device shown in FIG. 1. An agent permeable membrane 11, 21 (in FIGS. 1 and 2, respectively) is preferably a porous membrane. A contact electrode pair for electroporation 12, 22 is affixed to the agent permeable membrane 11, 21, such that the device of the first embodiment forms an electrode membrane. The contact electrode pair 12, 22 is shown with two comb-like electrodes in an interdigitated pattern (though the electrodes do not contact one another), but the invention is not limited to that form. A portion of the contact electrode pair 12, 22 is shown as protruding from the membrane 11, 21. However, the contact electrode pair 12, 22 can also be entirely embedded in the agent permeable membrane. This protruding portion of the contact electrode pair is a terminal for connecting the contact electrode pair 12, 22 to a power supply device (not shown).

The materials used to construct the membrane 11, 21 supporting the contact electrode pair 12, 22 are not particularly limited, but can be selected (e.g., heuristically) as desirable depending upon the type of therapeutic agent to be administered or the nature of the pharmaceutical composition containing a therapeutic agent. For example, when a water-soluble pharmaceutical composition or therapeutic agent is used, a hydrophilic membrane which does not have limited membrane permeability for that pharmaceutical composition is selected. If a lipid-soluble pharmaceutical composition or therapeutic agent is used, it would be desirable to use a hydrophobic membrane which does not have limited membrane permeability for that pharmaceutical composition. Similarly, it is desirable to use a porous membrane having pores which do not hamper the delivery of a therapeutic agent or pharmaceutical compositions being administered. A pore size of about 0.01 $\mu$m to 10 $\mu$m is preferred, and about 0.1 to 5 $\mu$m is more preferred in order to retain the pharmaceutical composition in the device, prevent leakage, and maintain a desirable drug permeation rate through the membrane. For example, the materials used for the membrane in various embodiments include, but are not limited to, porous or foam substances such as nylon, polyvinylidene fluoride, cellulose, nitro cellulose, polycarbonate, polysulfone, polyethylene, polypropylene, non-woven fabric, gauze, woven fabric, paper, cotton, polyethylene foam, polypropylene foam, polyvinyl acetate foam, polyorefine foam, polyamide foam, and polyurethane foam. These materials and chemical modifications and treatments thereof are provided as examples but the materials covered by the invention are not limited to these.

Examples of methods of affixation for the contact electrode pair 12,22 and the above-described membrane 11,21 supporting the contact electrode pair 12,22 include, but are not limited to, adhesion, printing, vapor deposition, and plating. Of these methods, printing is especially desirable because it can be easily controlled by techniques such as using a pattern or screen printing a form. Adhesion is also desirable as a simple method of integration.

The contact electrode pair 12, 22 is a pair of anode and cathode electrodes which are affixed on the permeable membrane 11, 21. It is desirable to have the distance between the two electrodes small in order to generate high voltage efficiency. However, there is the possibility of short circuits in the membrane 11, 21. Considering factors such as efficiency in applying electric pulses, simplicity of affixation, and accuracy of affixation, the distance will vary depending upon the affixation method used. In general, about 10 $\mu$m to 1 cm is preferable, about 50 $\mu$m to 5 mm is more preferred, and about 100 $\mu$m to 2 mm is yet more preferred.

The contact electrode pair 12, 22 is made from materials which are or can be made electrically conductive such as carbon, platinum, gold, titanium, aluminum, nickel, steel, silver, silver chloride, copper, copper chloride, or an alloy of one of these. Carbon, silver, and silver chloride are preferred because of their advantages for printing.

In use, the electrode membrane of the first embodiment is applied to a site of administration, preferably the skin or mucosa. A therapeutic agent is then applied to the agent permeable membrane. The porous nature of the agent permeable membrane brings the therapeutic agent into contact with the skin. An electric signal is applied utilizing electroporation such that the therapeutic agent is delivered through the skin. Alternately, the therapeutic agent could be pre-impregnated into the agent permeable membrane prior to application to the site of administration.

Figure 4A:
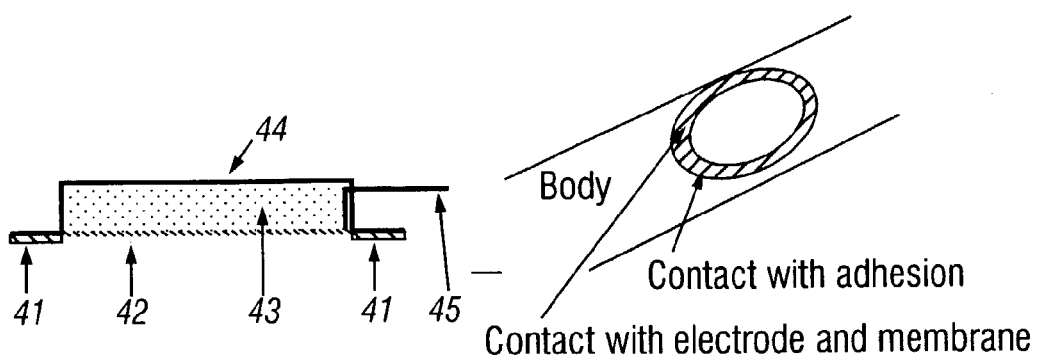
FIG. 4 shows a second embodiment of the invention.
Figure 4B:
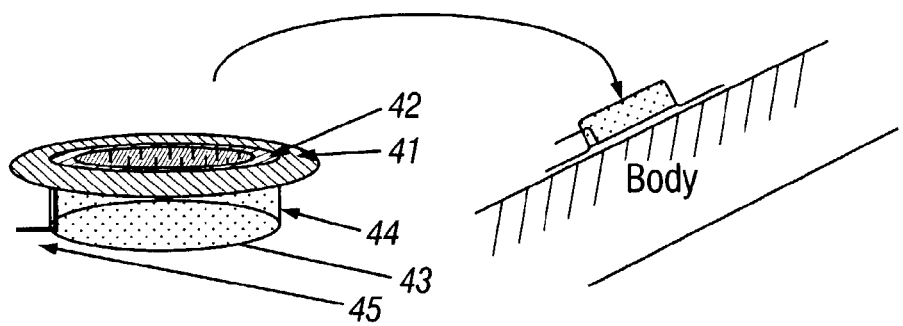

A second embodiment of the invention, as shown in FIG. 4, is a device for electroporation integrating the above-described electrode membrane. An adhesion layer 41 includes an adhesive for keeping the device in contact with skin or mucosa. An electrode membrane for electroporation 42, as described above and shown in FIGS. 1 and 2, is on a lower portion of the device. A pharmaceutical composition layer 43 contains a therapeutic agent to be administered. A casing 44 forms a reservoir which contains the pharmaceutical composition layer 43. A contact electrode terminal 45 for connecting a contact electrode pair (within the electrode membrane 42; see the contact electrode pair 12, 22 in FIGS. 1 and 2) to a power supply device (not shown) protrudes from the casing 44.

In use, a device according to the second embodiment is applied to a site of administration, held in place by the adhesive. The reservoir may already contain the pharmaceutical composition or the pharmaceutical composition may be added after application. Similar to the first embodiment, the pharmaceutical composition or therapeutic agent come into contact with the site of administration by permeating the agent permeable membrane. The therapeutic agent is delivered by applying an electric signal to the contact electrodes utilizing electroporation.

Figure 3:
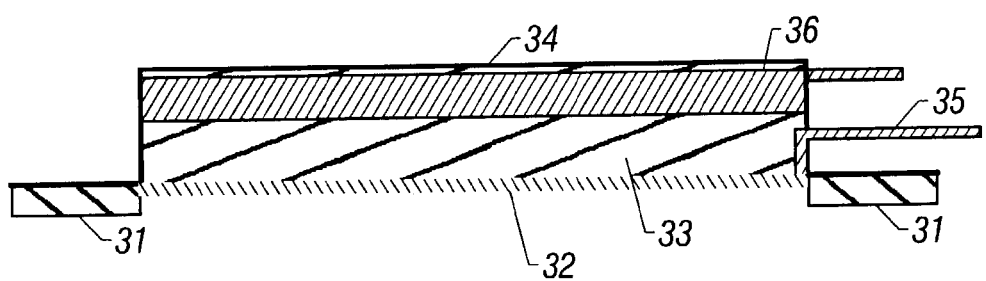
FIG. 3 shows a third embodiment of the invention which can jointly use electroporation and iontophoresis.

A third embodiment of the invention, as shown in FIG. 3, is a device which can jointly use electroporation and iontophoresis. An adhesion layer 31 includes an adhesive for keeping the device in contact with skin or mucosa. An electrode membrane for electroporation 32, as described above and shown in FIGS. 1 and 2, is on a lower portion of the device and contacts the site of administration 37. A pharmaceutical composition layer 33 contains a therapeutic agent to be administered. A casing 34 forms a reservoir which contains the pharmaceutical composition layer 33. A contact electrode terminal 35 for connecting a contact electrode pair (within 32; the contact electrode pair 12, 22 in FIGS. 1 and 2) to a power supply device (38) protrudes from the casing 34. The above components are similar to those of the second embodiment shown in FIG. 4. However, the third embodiment also has an iontophoretic electrode (anode or cathode) 36 for iontophoresis located between the electrode membrane 32 and the casing 34. A counter electrode (37) which is opposite to the iontophoretic electrode (i.e., if the iontophoretic electrode 36 is an anode, the counter electrode is a cathode) is also attached to the skin or mucosa 39 to complete an electrical circuit for iontophoresis.

In use, a device according to the third embodiment is applied to a site of administration, held in place by the adhesive. The reservoir may already contain the pharmaceutical composition or the pharmaceutical composition may be added after application. Similar to the first embodiment, the pharmaceutical composition or therapeutic agent come into contact with the site of administration by permeating the agent permeable membrane. The therapeutic agent is delivered by applying an electric signal to the contact electrodes and another electric signal to the iontophoretic electrode thus utilizing electroporation and iontophoresis jointly.

The casing 34, 44 (in FIGS. 3 and 4, respectively) is preferably made from materials such that the casing 34, 44 is elastically deformable (i.e., flexible yet shape-retentive) and water-resistant. For example, polymers such as polyvinylidene chloride, polyvinyl chloride, polyorefine, polyester, polystyrene, poly acryl, polyamide, polyoxymethylene, polyphenylenesulfuramide, polyamide, polyimide, polyacrylonitrile, polyetherketone, polyethersulfone, polysulfone, etherimide, polybutadiene, and isoprene or copolymers of these materials may be used, though the invention is not limited to them. The casing preferably is made from the above materials which are in a film form (e.g., a backing film) or have been manufactured into a shape. The thickness is not especially limited, but a thickness of about 5 to 250 $\mu$m provides desirable shape-retention and flexibility.

The administered pharmaceutical composition delivered by the device includes any composition which would have a desired biological effect. The composition is contained in the pharmaceutical composition layer 33, 43 and preferably includes but is not limited to, in addition to a base component (such as a therapeutic agent), electrolytes, absorption accelerants, stabilizers, pH buffers, thickeners, detergents, emulsifiers, ion exchange resins, ion exchange membranes, or nonwoven fabrics.

The casing 34,44 and electrode membrane 32,42 are preferably sealed using a process such as heat sealing.

When an iontophoretic electrode 36 (anode or cathode) is integrated, the iontophoretic electrode 36 may be a polarized electrode made from materials such as carbon, platinum, gold, or titanium or an unpolarized electrode, but an unpolarized electrode is more preferred. An unpolarized anode electrode preferably includes silver or copper, but silver is more preferred. An unpolarized cathode electrode preferably includes silver chloride or copper chloride, but silver chloride is more preferred.

For electroporation, an electric signal is applied to the contact electrode pair such that a voltage differential is created preferably ranging from about 10 to 2000 V/cm. About 50 to 1000 V/cm is more preferred and about 50 to 500 V/cm is yet more preferred. A recommended pattern of applying the electric signal is one such as exponential logarithmic wave forms or square wave forms, but is not limited to those. The electric signal for electroporation is preferably applied one or more times.

For iontophoresis, an electric signal is applied to the iontophoretic electrode pair (the iontophoretic electrode 36 of FIG. 3 and the counter electrode), preferably as a pulsed current signal from about 0.01 to 10 mA, and more preferably about 0.01 to 5 mA. A voltage differential is created preferably from about 0.1 to 50 V, more preferably about 1 to 30 V, and yet more preferably about 3 to 15 V. The pulsed current signal has a pulse frequency of pulse depolarization preferably about 100 Hz to 1000 KHz, more preferably about 1 to 500 KHz, and yet more preferably about 10 to 300 KHz. The pulsed current signal has a duty cycle with an ON/OFF ratio preferably about 1 to 99%, more preferably about 10 to 80%, and yet more preferably about 15 to 50%. Waveforms for applying electric current, direct current, pulse, and pulse depolarization, can be freely set.

As described above, the pharmaceutical composition preferably includes a therapeutic agent (such as a biologically active substance) to achieve the desired therapeutic effect upon delivery (e.g., to ameliorate some disorder). The therapeutic agents used in the present invention are not restricted in type. Examples include, but are not limited to: analgesics such as morphine, fentanyl, pethidine, codeine, buprenorphine, butorphanol, eptazocine, or pentazocine; peptides/proteins such as insulin, calcitone, calcitonin gene-related peptide, vasopressin, desmopressin, protirelin (TRH), adrenocorticotropic hormone (ACTH), luteinizing hormone releasing hormone (LH-RH), growth hormone releasing hormone (GRH), nerve growth factor (NGF) or other releasing factors, angiotensin, parathyroid hormone (PTH), thyroid-stimulating hormone (TSH, thyrotropin), follicle stimulating hormone (FSH), luteinizing hormone (LH), prolactin, serum gonadotrophin, human chorionic gonadotrophin (HCG), human menopausal gonadotrophin (HMG), human growth hormone, somatostatin, somatomedin, glucagon, oxytocin, gastrin, secretin, endorphin, enkephalin, endothelin, cholecystokinin, neurotensin, interferon, interleukin, transferrin, erythropoietin (EPO), superoxide dismutase (SOD), granulocyte colony stimulating factor (G-CSF), vasoactive intestinal peptide (VIP), muramyldipeptide, urogastrone, or human atrial natriuretic peptide (h-ANP); tranquilizers such as carbamazepine, chlorpromazine, diazepam, or nitrazepam; antineoplastic drugs such as bleomycin, doxorubicin, 5-fluorouracil, or mitomycin; cardiotonics such as digitalis, digoxin, or digitoxin; sex hormones such as estradiol or testosterone; or hypotensive drugs such as reserpine or clonidine. Furthermore, antisense DNA and oligonucleotides such as triple helix-forming oligonucleotide can also be used.

Using the techniques described above, the present invention effectively delivers a therapeutic agent via the skin or mucosa. In conventional electroporation electrodes, typically an electrode pair was attached to a film which was not permeable to substances. Medicinal solution was applied to a site such as skin. The electrode film was then placed over the site and electric field pulses applied. In cases where multiple administrations were necessary, the procedure had to be repeated. It could not be done in one application. When jointly using iontophoresis, after applying medicinal solution to an administration site, the site was covered by an electrode film. After electroporation was performed, the electrode film was removed. An electrode for iontophoresis was then applied to the site and an electric current for iontophoresis was applied. It was necessary to perform each step of this operation. When electroporation was again to be applied, the process was repeated. The process could not be completed in one physical application of electrodes.

The present invention not only permits only one application of a device including an electrode membrane to administer a therapeutic agent, but also continuous administration has been made possible. Even when jointly using iontophoresis, only a single affixation of a device integrating an electrode membrane (for electroporation) and an electrode for iontophoresis is necessary. Furthermore, when affixing the electrodes, electroporation and iontophoresis are not limited to a single application. Accordingly, by using a device according to the present invention as described above, a device is provided which enables electroporation alone or electroporation in conjunction with iontophoresis and can be used for multiple applications over extended periods of time. The present invention can be used broadly throughout the medical field in the administration of therapeutic agents.

Examples of implementations of the present invention are given below to illustrate the use and efficacy of the present invention, but the present invention is not limited to the forms described below.

In Experiment Example 1, ease of administration is compared when sodium benzoate is administered using a prior art electrode pair, using an electrode membrane of the present invention, and using a device created using an electrode membrane of the present invention. Compliance was compared using the number of operations as an indicator.

In Experiment Example 1—1, an electrode membrane of the present invention was used. An electrode membrane was created by laminating a silver electrode pair on a Durapore SVLP™ membrane (made by Millipore™; pore diameter=3.0 μm) (the same configuration as shown in FIGS. 1 and 2). Adhesive was applied to the outer circumference thereon, and the electrode membrane was affixed to the skin. Medicine (an aqueous solution of sodium benzoate, 100 mg/ml) on the electrode membrane was administered at 200 μl every hour for three hours (a total of 600 μl). Each time the medicinal solution was administered an electric field pulse of 200 V/cm was applied from a electroporation power supply device (made by BTX™). The number of operations was counted.

In Experiment Example 1-2, a device including an electrode membrane of the present invention was used. A device as shown in FIG. 4 was created using an electrode membrane as described in Experiment Example 1—1. 600 μl of medicinal solution were contained within the device. The device containing this electrode membrane was affixed to the skin and every hour an electric field pulse of 200 V/cm was applied from a electroporation power supply device (made by BTX™). The number of operations was counted.

In Comparison Example 1, a prior art electrode film was used. A presently marketed electrode film was used (BT454-2P™ by BTX™). A medicinal solution (an aqueous solution of sodium benzoate, 100 mg/ml) was applied to the skin and then that area was covered by the electrode film. An electric field pulse of 200 V/cm was applied from an electroporation power supply (made by BTX™). These operations were repeated three times, and the number of operations was counted.

Figure 5:
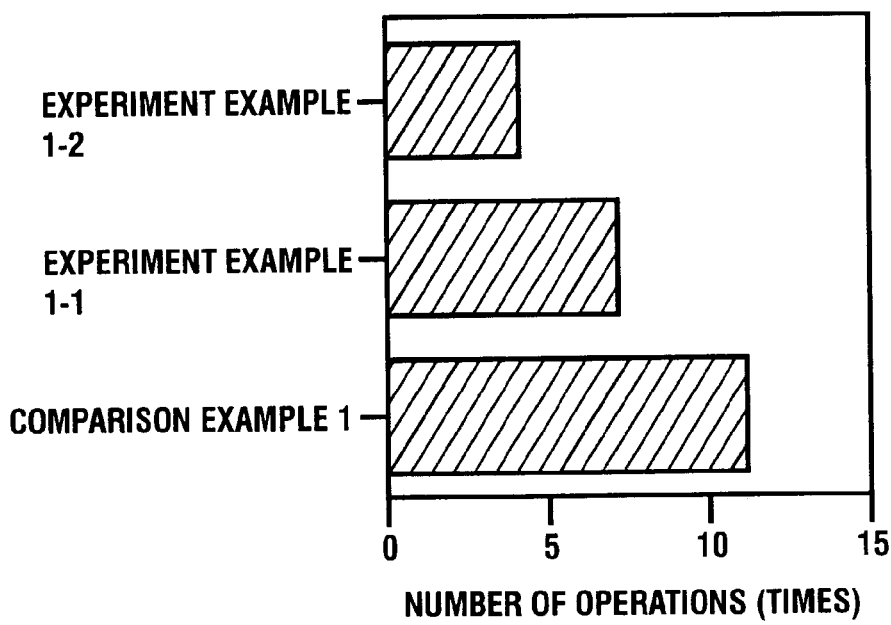
FIG. 5 is a chart showing a comparison of numbers of operations from three different applications of electroporation (Experiment Example 1-2, Experiment Example 1—1, Comparison 1).

The results of Experiment Example 1 are shown in FIG. 5. Using an electrode membrane of the present invention (Experiment Example 1—1) required a total of seven operations: (1) affixing the electrodes; (2) applying the medicinal solution; (3) applying voltage; then after waiting one hour, (4) applying the medicinal solution; (5) applying voltage; then after waiting one hour, (6) applying the medicinal solution; and (7) applying voltage.

Applying a device including an electrode membrane of the present invention (Experiment Example 1-2) required a total of four operations: (1) affixing the device; (2) applying voltage; then after waiting one hour, (3) applying voltage; and then after waiting one hour, (4) applying voltage.

Using a prior art electrode film and administering it using conventional methods (Comparison Example 1) required a total of eleven operations: (1) applying the medicinal solution; (2) affixing the electrodes; (3) applying voltage; then after waiting one hour, (4) peeling off the electrodes; (5) applying the medicinal solution; (6) affixing the electrodes; (7) applying voltage; then after waiting one hour, (8) peeling off the electrodes; (9) applying the medicinal solution; (10) affixing the electrodes; and (11) applying voltage.

As shown by the number of operations above, administration becomes simpler using an electrode membrane of the present invention. When practical application is considered, when patients administer therapeutic agents at home, the administration form of Comparison Example 1 is not practical. On the other hand, patients can easily perform the administration at home using a device such as the one in Experiment Example 1-2.

In Experiment Example 2, ease of administration is compared when electroporation and iontophoresis are jointly used in administering lidocaine hydrochloride using an electrode membrane of the present invention and using a conventional electrode film. Compliance was compared using the number of operations as an indicator.

In Experiment Example 2-1, 200 μl of an aqueous solution of lidocaine hydrochloride (5%) were added to a device including a presently marketed electrode for iontophoresis (tansQ™ by Iomed™). The device was created by integrating the iontophoretic electrode and the electrode membrane created in Experiment Example 1—1 according to the present invention as shown in FIG. 3. This device, as well as a counter electrode (tansQ™ by Iomed™) were applied to the skin. The electrode pair for iontophoresis (the positive electrode is on the medicinal side at the site of administration, the negative electrode is the counter electrode) was connected to an iontophoresis power supply device. The electroporation electrode pair was connected to an electroporation power supply device. 200 V/cm was applied from the electroporation power supply device, and then 0.1 mA/cm$^2$ was applied from the iontophoresis power supply device for one hour. After one hour, 200 V/cm was again applied from the electroporation power supply device, and then 0.1 mA/cm$^2$ was again applied from the iontophoresis power supply device for one hour under the same conditions. The number of operations was counted.

In Experiment Example 2—2, a similar operation as in Experiment Example 2-1 was performed. However, initially the start and stop times for application of electric signals for iontophoresis and electroporation application times were set in a timer and so were performed automatically. The number of operations was counted.

In Comparison Example 2, 200 μl of an aqueous solution of lidocaine hydrochloride (5%) were added to a presently marketed device including an electrode for iontophoresis (tansQ™ by Iomed™). Upon the skin, electroporation was applied using a conventional electrode pair (at 200 V/cm). The iontophoresis device containing lidocaine was applied to the skin and electric current was applied for one hour. After one hour, electroporation was applied, and then once again iontophoresis was applied for one hour. The number of operations was counted.

Figure 6:
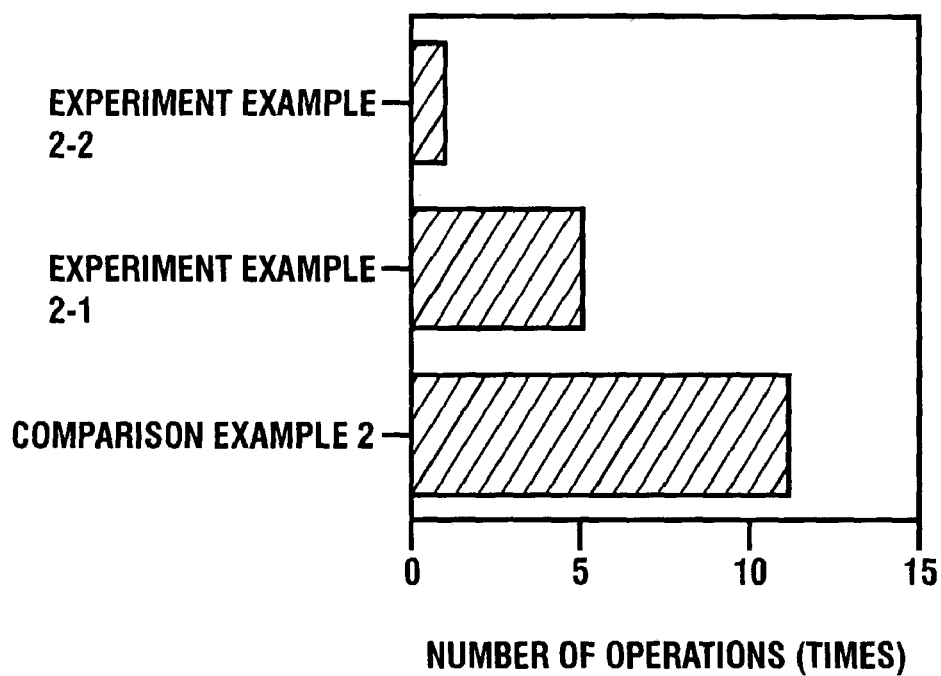
FIG. 6 is a chart showing a comparison of numbers of operations from applications of joint uses of electroporation and iontophoresis (Experiment Example 2—2, Experiment Example 2-1, Comparison 2).

The results of Experiment Example 2 are shown in FIG. 6. Experiment Example 2-1 required a total of five operations: (1) affixing the device; (2) applying electroporation voltage; (3) applying iontophoresis electrical current; (4) applying electroporation voltage; and (5) applying iontophoresis electrical current.

In Experiment Example 2—2, because the application of electroporation voltage and iontophoresis electrical current of Experiment Example 2-1 was able to be performed automatically using a timer, the number of operations was reduced leaving only a single operation to perform (affixing the device).

By contrast, Comparison Example 2 required a total of eleven operations: (1) affixing the electrode film; (2) applying electroporation voltage; (3) removing the electroporation electrodes; (4) affixing the iontophoresis device containing lidocaine; (5) applying iontophoresis electrical current; (6) removing the iontophoresis device containing lidocaine; (7) affixing the electrode film; (8) applying electroporation voltage; (9) removing the electroporation electrodes; (10) affixing the iontophoresis device containing lidocaine; (11) applying iontophoresis electrical current.

Using the present invention, it is not necessary to remove the electroporation electrodes from the site of application each time a therapeutic agent is administered. With one application of an electrode membrane, multiple administrations of therapeutic agents and continuous administration of therapeutic agents over long periods of time are possible. Furthermore, using the device of the present invention, a device is created which integrates both the electrode membrane for electroporation and the electrode for iontophoresis into a single device, making it is possible to have a device which jointly uses electroporation and iontophoresis.

A number of embodiments of the present invention have been described. Nevertheless, it will be understood that various modifications may be made without departing from the spirit and scope of the invention. Accordingly, other embodiments are within scope of the following claims.

What is claimed is:

1. A method of in vivo administration of a therapeutic agent including the following steps: (a) contacting a device which includes an agent permeable membrane having a pair of contact electrodes to a site of administration such that the agent permeable membrane directly contacts the site of administration, a casing attached to the agent permeable membrane forming a reservoir, a pharmaceutical composition including the therapeutic agent where the pharmaceutical composition is contained in the reservoir, an iontophoretic electrode which is located in the reservoir; (b) contacting a counter electrode to a second site; (c) applying a first electric signal to the contact electrodes; and (d) applying a second electric signal to the iontophoretic electrode.

2. The method of claim 1 where the second electric signal is a pulsed current signal from about 0.01 to 10 mA.

3. The method of claim 2 where the pulsed current signal is from about 0.01 to 5 mA.

4. The method of claim 1 where the second electric signal creates a voltage differential from about 0.1 to 50 V between the iontophoretic electrode and the counter electrode.

5. The method of claim 4 where the voltage differential is from about 1 to 30 V.

6. The method of claim 5 where the voltage differential is from about 3 to 15 V.

7. The method of claim 1 where the second electric signal is a pulse depolarization signal at a pulse frequency from about 100 Hz to 1000 KHz.

8. The method of claim 7 where the pulse frequency is from about 1 to 500 KHz.

9. The method of claim 8 where the pulse frequency is from about 10 KHz to 300 KHz.

10. The method of claim 1 where the second electric signal has a duty cycle with an ON/OFF ratio between about 1 and 99%.

11. The method of claim 10 where the duty cycle is between about 10 and 80%.

12. The method of claim 11 where the duty cycle is between about 15 and 50%.

* * * * *